United States Patent
Schroer, Jr.

(10) Patent No.: US 10,188,563 B2
(45) Date of Patent: Jan. 29, 2019

(54) ABSORBENT ARTICLES WITH PULPLESS RIFFLED CORE

(71) Applicant: DSG TECHNOLOGY HOLDINGS LIMITED, Tortola (VG)

(72) Inventor: Charles F. Schroer, Jr., Raleigh, NC (US)

(73) Assignee: DSG Technology Holdings Ltd., Kwai Chung, N.T. (HK)

(*) Notice: Subject to any disclaimer, the term of this patent is extended or adjusted under 35 U.S.C. 154(b) by 0 days.

(21) Appl. No.: 14/418,033

(22) PCT Filed: Mar. 13, 2014

(86) PCT No.: PCT/US2014/026148
§ 371 (c)(1),
(2) Date: Jan. 28, 2015

(87) PCT Pub. No.: WO2014/151639
PCT Pub. Date: Sep. 25, 2014

(65) Prior Publication Data
US 2016/0051420 A1 Feb. 25, 2016

Related U.S. Application Data

(60) Provisional application No. 61/791,609, filed on Mar. 15, 2013.

(51) Int. Cl.
*A61F 13/53* (2006.01)
*A61F 13/537* (2006.01)
(Continued)

(52) U.S. Cl.
CPC ...... *A61F 13/537* (2013.01); *A61F 13/49015* (2013.01); *A61F 13/49019* (2013.01);
(Continued)

(58) Field of Classification Search
CPC ............ A61F 13/5323; A61F 13/53436; A61F 2013/53051
See application file for complete search history.

(56) References Cited

U.S. PATENT DOCUMENTS 4,840,692 A 6/1989 Kamstrup-Larsen
5,843,063 A * 12/1998 Anderson ......... A61F 13/15203
428/218

(Continued)

FOREIGN PATENT DOCUMENTS

JP 2000333986 A 12/2000
JP 2006068551 A 3/2006
(Continued)

OTHER PUBLICATIONS

International Search Report and Written Opinion issued in PCT Application No. PCT/US2014/026148, dated Jul. 20, 2014 [8 pages].
(Continued)

*Primary Examiner* — Peter S Vasat
(74) *Attorney, Agent, or Firm* — Alberto Q. Amatong, Jr.; Amatong McCoy LLC

(57) ABSTRACT

Disposable absorbent articles comprising absorbent cores are presented. In one embodiment, an absorbent core may comprise a riffled substrate comprising a plurality of peaks and a plurality of troughs, a flat substrate coupled to the riffled substrate, and superabsorbent polymer disposed between the riffled substrate and the flat substrate, wherein the footprint of the riffled substrate is substantially the same as the footprint of the flat substrate, and wherein the surface area of the riffled substrate is greater than the surface area of the flat substrate.

32 Claims, 11 Drawing Sheets

(51) Int. Cl.
*A61F 13/49* (2006.01)
*A61F 13/532* (2006.01)
*A61F 13/534* (2006.01)
*A61F 13/56* (2006.01)

(52) U.S. Cl.
CPC .... *A61F 13/5323* (2013.01); *A61F 13/53436* (2013.01); *A61F 13/5622* (2013.01); *A61F 13/5638* (2013.01); *A61F 2013/53051* (2013.01)

(56) References Cited

U.S. PATENT DOCUMENTS

| | | |
|---|---|---|
| 8,268,424 B1 | 9/2012 | Suzuki et al. |
| 2004/0236299 A1* | 11/2004 | Tsang ................ A61F 13/15756 604/385.24 |
| 2006/0184146 A1 | 8/2006 | Suzuki |
| 2008/0103466 A1 | 5/2008 | Ehrnsperger et al. |
| 2010/0057032 A1 | 3/2010 | Hardegree |
| 2010/0063470 A1* | 3/2010 | Suzuki .................. A61F 13/53 604/367 |
| 2011/0046597 A1 | 2/2011 | Mizutani et al. |
| 2012/0071852 A1 | 3/2012 | Tsang et al. |
| 2013/0018349 A1* | 1/2013 | Takatori .............. A61F 13/5323 604/372 |

FOREIGN PATENT DOCUMENTS

| | | | |
|---|---|---|---|
| JP | 2009119022 A | 6/2009 | |
| JP | 2011130798 A | 7/2011 | |
| JP | 2011135921 A | 7/2011 | |
| JP | WO 2011118409 A1 * | 9/2011 | ......... A61F 13/5323 |
| WO | WO0041663 | 7/2000 | |

OTHER PUBLICATIONS

Notification of Transmittal of International Preliminary Report on Patentability dated May 22, 2015 (issued in PCT Application No. PCT/US14/26148) [16 pages].

* cited by examiner

ABSORBENT ARTICLES WITH PULPLESS RIFFLED CORE

CROSS-REFERENCE TO RELATED APPLICATION

This application claims the benefit of U.S. Provisional Application No. 61/791,609, filed Mar. 15, 2013, which is incorporated by reference in its entirety.

FIELD OF THE INVENTION

The present invention relates generally to disposable absorbent articles employing absorbent composites. Disposable absorbent articles include diapers, training pants, adult incontinence products, bodily exudates absorbing products, feminine hygiene products, and other absorbent products (collectively "disposable absorbent articles").

The principal elements that typically make up the disposable absorbent articles described above are a liquid-permeable inner layer (or topsheet), a liquid-impermeable outer layer (or backsheet), and an absorbent core sandwiched between the inner and outer layers. Elasticized barrier leg cuffs, gathering components, and waistbands are often employed to provide leakage prevention by enhancing the fit of the absorbent article about the thighs and waist of the user. For example, elastic members may be positioned longitudinally along the article, generally outboard of the absorbent core to effect a seal around the legs, buttocks, or both of the user. In addition, several elastic members (e.g., in the form of elongated elastic threads or strands) may be positioned laterally throughout the waist regions (including side waist regions) of the disposable absorbent article to allow the article to stretch when it is put on and then during wear. In this way, the article can stretch to accommodate variations of waist size and leg size of the user, while fitting snugly about the waist and legs and without sagging.

Prior disposable absorbent articles typically employ three basic structural elements: a topsheet that forms the inner surface, a backsheet that forms the outer surface, and an absorbent core that is interposed between the topsheet and the backsheet. The topsheet is designed to allow liquid to pass from outside the absorbent article through the topsheet and into the absorbent core. The topsheet may be made out of a range of liquid and vapor permeable hydrophilic or hydrophobic materials. The permeability of the topsheet can be increased by using surface activation agents ("surfactants"). Surfactants lower the surface energy or the contact angle of the liquid-solid interface and facilitate the liquid's passage through the topsheet.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmittable non-woven material such as spunbond, melt-blow, spun-bond ("SMS"); spun-bond, melt-blown, melt-blown, spun-bond ("SMMS"); micro-, nano-, or splittable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Most of a diaper's thickness comes from the absorbent core.

SUMMARY OF THE INVENTION

Disposable absorbent articles are presented. In one embodiment, a disposable absorbent article is presented comprising: a central body including an absorbent core, a front longitudinal edge, and a rear longitudinal edge opposite said front longitudinal edge, wherein said front and rear edges of said central body define, at least partially, front and rear waist portions respectively and said central body is characterized by a longitudinal centerline extending across said front and rear edges; and wherein the absorbent core comprises: a riffled substrate comprising a plurality of peaks and a plurality of troughs; a flat substrate coupled to the riffled substrate; and superabsorbent polymer disposed between the riffled substrate and the flat substrate; wherein the footprint of the riffled substrate is substantially the same as the footprint of the flat substrate; and wherein the surface area of the riffled substrate is greater than the surface area of the flat substrate.

In specific embodiments, the disposable absorbent article is configured such that the superabsorbent polymer is adhered to at least one of the riffled substrate or the flat substrate with an adhesive.

In other embodiments, the superabsorbent polymer is bound to at least one of the riffled substrate or the flat substrate with a binder.

In still other embodiments, the disposable absorbent article further comprises an acquisition layer coupled to the absorbent core.

In other embodiments, the disposable absorbent article further comprises a distribution layer coupled to and between the acquisition layer and the absorbent core.

In various embodiments, the riffled substrate or the flat substrate may comprise tissue. In other embodiments, the riffled substrate or the flat substrate may comprise nonwoven fabric.

In other embodiments, any of the above disposable absorbent articles further comprise a pair of elasticized side panels distinct from said central body and extending longitudinally and adjacent opposite longitudinal sides of said central body a length sufficient to wrap around the legs of a user of the disposable absorbent article when worn, each said side panel having a front latitudinal edge, a rear latitudinal edge opposite said front latitudinal edge, a proximal longitudinal periphery edge, a portion of which is at least co-extensive with said central body, a distal longitudinal periphery edge, and at least one fastening portion for fastening said front and rear waist portions of said central body when the disposable absorbent article is worn by a user; wherein the distal longitudinal periphery edge of the side panels are generally parallel to one another along the length of the side panels; wherein each elasticized side panel comprises an elastic element, the elastic element providing a direction of stretch to said side panel that is generally parallel to said longitudinal centerline; wherein said elastic element extends longitudinally past a corresponding said front or rear latitudinal edges of said central body, wherein said front latitudinal edge of said side panel is positioned closer to said front waist portion of said central body than to said rear waist portion of said central body; wherein each said side panel includes a front or rear fastening portion formed by said side panel extending longitudinally past a corresponding said front or rear latitudinal edges of said central body, said front or rear fastening portion being constructed for fastening said front and rear waist portions of said central body when the disposable absorbent article is worn by a user; wherein each said fastening portion includes a first fastening element adapted to engage a second fastening element on said central body, wherein the first fastening element is located within the fastening portion and is longitudinally positioned past the latitudinal front or rear edge of said central body such that the fastening element is within the fastening portion in a section thereof which is not coextensive with the central body, and wherein said fastening element is in longitudinal alignment with an elasticized side panel; wherein when the absorbent article is disposed in a relaxed, open and generally flat condition said central body, elasticized side panels and fastening portions all occupy a single plane; wherein the fastening portions are integral to or permanently affixed to the disposable absorbent article; wherein the elastic elements of said side panels disposed along said length of said side panel to impart elasticity therealong in a longitudinal direction sufficient to cause said side panels to engage the legs of the user when the disposable article is worn; and wherein the amount of said imparted elasticity generally increases from the front to the rear of the legs, said increase in elasticity configured to provide tension at least around said front waist portion when worn.

In still other embodiments, the side panels of any of the any of the above disposable absorbent articles further include fastening portions of substantially zero elastication positioned longitudinally between said front latitudinal edges of said side panels and said elastic elements.

In other embodiments, the fastening portions in longitudinal alignment with said elastic elements.

In still other embodiments, regions of elastication form a gradient of varying tension along the said portion of said length that is wrapped about the legs of a user when said disposable absorbent article is worn.

In certain embodiments, the elastic elements disposed along said length of said side panel of certain of the above absorbent articles are configured to impart elasticity therealong in a longitudinal direction comprise a plurality of elastomeric strands and wherein the regions of elastication are defined by a) the presence of at least one elastomeric strand per region and b) a greater number of elastomeric strands in the side panel at the rear most region than the front most region of the side panel.

Certain embodiments of the above absorbent articles comprise one or more intermediate side panel regions between the front most and rear most regions, each intermediate region having, from front to rear, a greater number of elastomeric strands than the previous region.

In other embodiments of certain of the above absorbent articles, said elastic elements are positioned such that the elasticity of said side panel generally increases in the direction from said front edge of said side panel to said rear edge of said side panel.

In various embodiments of the above disposable absorbent articles, said elastic elements are positioned such that a region of maximum elasticity of said side panel is provided in a vicinity of said rear edge of said side panel.

In various embodiments of the above disposable absorbent articles, said region of maximum elasticity is adjacent said rear edge of said central body.

In various embodiments of the above disposable absorbent articles, said elastic element is selected from the group of elastic elements consisting of: solid elasticizing film; liquid-applied elastomer; elastomeric strand; elastomeric ribbon; rubber; elastic foam; and combinations thereof.

In various embodiments of the above disposable absorbent articles, said elastic elements are elastomeric strands.

In various embodiments of the above disposable absorbent articles, each said side panel includes a greater number of elastomeric strands in the vicinity of said rear edge of said side panel than in the vicinity of said front edge of said side panel.

In various embodiments of the above disposable absorbent articles, each said side panel includes thicker elastomeric strands in the vicinity of said rear edge of said side panel than in the vicinity of said front edge of said side panel.

In various embodiments of the above disposable absorbent articles, each said side panel includes a greater concentration of elastomeric strands in the vicinity of said rear edge of said side panel than in the vicinity of said front edge of said side panel.

In various embodiments of the above disposable absorbent articles, said side panel include regions provided with elastomeric strands and fastening portion without elastic strands.

In various embodiments of the above disposable absorbent articles, said elastomeric strands are disposed between two layers of nonwoven material, said elastomeric strands arc attached to the two layers of nonwoven material along the length of the elastomeric strands.

In various embodiments of the above disposable absorbent articles, said fastening portion is a rear fastening portion that extends past said corresponding rear edge of said central body.

In various embodiments of the above disposable absorbent articles, said elastic elements are positioned such that a region of maximum elasticity of said side panel is provided in a vicinity of said rear fastening portion.

In various embodiments of the above disposable absorbent articles, central body includes a topsheet and a backsheet, said side panels being formed by extensions of said topsheet and said backsheet.

In various embodiments of the above disposable absorbent articles, said fastening portion has an outward facing periphery edge, a latitudinal periphery edge and an inward facing periphery edge, said inward facing and outward facing periphery edges are in parallel alignment with said longitudinal centerline; and the outward facing, longitudinal periphery edge of said fastening portion is colinear with the longitudinal periphery edge of said side panel and the inward facing longitudinal periphery edge of said fastening portion is extended perpendicularly from the latitudinal front or rear edge of said central body.

The term "coupled" is defined as connected, although not necessarily directly, and not necessarily mechanically. Two items are "couplable" if they can be coupled to each other, and, when coupled, may still be characterized as "couplable." Unless the context explicitly requires otherwise, items that are couplable are also decouplable, and vice-versa. One non-limiting way in which a first structure is couplable to a second structure is for the first structure to be configured to be coupled (or configured to be couplable) to the second structure.

The terms "a" and "an" are defined as one or more unless this disclosure explicitly requires otherwise.

The term "substantially" and its variations (e.g., "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, an absorbent article that comprises an absorbent core has at least an absorbent core, but may have additional elements such as an acquisition layer or a distribution layer.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

The embodiments of the present absorbent articles in FIGS. 1-15 are drawn to scale.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

The term "absorbent article" or "absorbent garment" with which the present invention is associated, includes various types of disposable articles and garments which are placed against or in proximity to the body of the wearer so as to absorb and contain various bodily exudates, bodily fluid, or biofluid.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
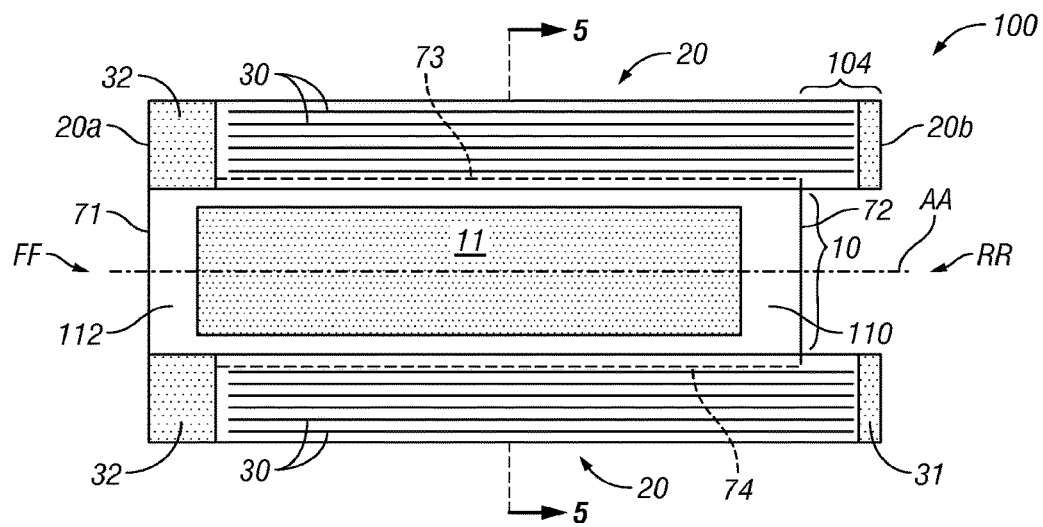
FIG. 1 is a plan view of an inside face of an embodiment of disposable absorbent article in a generally flat, open condition, according to the present invention.
Figure 2:
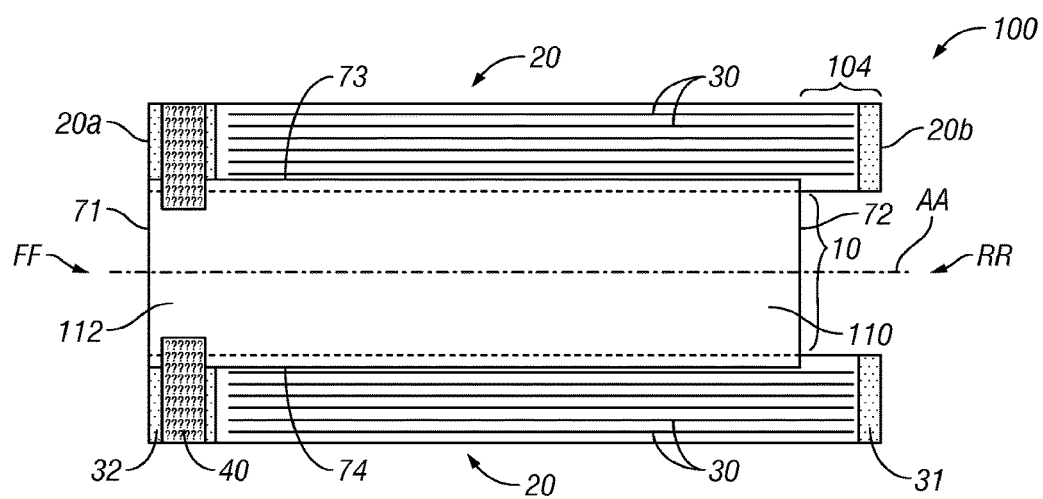
FIG. 2 is a plan view of an outside face of the disposable absorbent article of FIG. 1.

FIGS. 1 and 2 depict the absorbent article 100 in a generally flat, open condition, i.e., the form possibly taken by the article prior to being worn by the user or during a later stage in the manufacturing process. To facilitate the description of the various embodiments, the absorbent article 100 is referred to as having a centrally bisecting longitudinal centerline AA. The article 100 also has a front "FF" and rear "RR" which correspond to the positions taken by the article components in respect to the body of the user when worn.

The inventive disposable absorbent article 100 is preferably of a three-piece/element construction consisting of a central body or absorbent assembly 10 and two longitudinal elastic side panels or stretch panels 20 disposed adjacent opposite lateral sides of the absorbent assembly 10. These longitudinally extending stretch panels 20 may be separately attachable to the absorbent assembly 10 as discussed below.

As will be shown below, the stretch panels 20 provide a sealing function in a manner similar to that associated with conventional barrier leg cuffs and leg gathers. Moreover, the stretch panels 20 according to the invention provide a waist fastening function and a waist or waistband tensioning function for the disposable absorbent article.

Referring also to FIGS. 5A-5E, absorbent assembly 10 preferably includes an absorbent core 11, a nonwoven liquid-permeable topsheet 12, and a liquid-impermeable backsheet 13. Absorbent assembly 10 may also include an acquisition or surge layer 14, preferably situated between the core 10 and the topsheet 12. The acquisition layer 14 functions to acquire exudes and draw them away from the body of a wearer. In still other embodiments, absorbent assembly 10 may comprise distribution layer 15. Distribution layer 15 acts to spread out and distribute liquid flow over the core surface. Materials suitable for each of the core 11, topsheet 12, backsheet 13, acquisition layer 14, and distribution layer 15 and the basic configuration of the absorbent assembly 10 are generally known in the art. Descriptions of some materials and configurations suitable for use with the present invention are found in PCT International Application WO 00/03670 (published Jan. 27, 2000), hereby incorporated by reference and made a part of the present disclosure.

Topsheet 12 is preferably soft, compliant, exhibits good strikethrough and a reduced tendency to rewet from a liquid pervious material. Topsheet 12 is placed in close proximity to the skin of the wearer when article 100 is worn. In this way, topsheet 12 permits bodily discharges to rapidly penetrate it so as to flow toward core 11 more quickly, but not allowing such discharges to flow back through topsheet 12. Topsheet 12 may be constructed from any one of a wide range of liquid and vapor permeable hydrophilic materials. The surface(s) of topsheet 12 may be treated with a surfactant so as to facilitate liquid transfer therethrough, especially at a central zone or area of topsheet 12 located over the core and an inner surface of the core. Topsheet 12 may also be coated with a substance having rash preventing or rash reducing properties (e.g., aloe vera). In certain embodiments, topsheet 12 comprises a single unitary material, while in other embodiments topsheet 12 comprises multiple different materials which vary across the width of topsheet 12. Such a multiple piece design allows for creation of preferred properties and different zones of topsheet 12.

Referring again to FIG. 1, the absorbent assembly 10 has an extended front longitudinal edge 71, a rear longitudinal edge 72, and two side lateral edges 73, 74. The front and rear edges 71, 72 form the longitudinal boundaries and, thus, define, at least partially, front and rear waist portions 112, 110 respectively.

One of ordinary skill in the relevant consumer product art will understand that various aspects of the present invention may be applied to other disposable absorbent articles and garments, and more particularly, to disposable absorbent articles other than disposable diapers. The present invention is not intended to be limited to the structures and manufacturing methods specifically described and illustrated herein.

The stretch panels 20 can be constructed by extending the topsheet 12 and backsheet 13 about a suitable elastomeric element 30. Alternatively, the stretch panels 20 may be constructed from a separate elastomeric material or assembly such as a longitudinal machine direction elastic (MDEL) stretchband 21, that is attached to the absorbent assembly 10. The stretch panel 20 is further characterized by a front longitudinal edge 20a that is positioned on the same end of the article 100 as the front waist portion 112 and a rear longitudinal edge 20b that is positioned on the same end of the article 100 as the rear waist portion 110. In one aspect of the invention, the length and/or position of the stretch panel 20 is such that the front or rear longitudinal edge 20a or 20b of the stretch panel 20 extends beyond the corresponding front or rear longitudinal edge 71 or 72 of the absorbent assembly 10. This extension provides a portion 104 of the stretch panel 20 that advantageously protrudes and extends beyond the corresponding front or rear longitudinal edge 71 or 72 of the absorbent assembly 10.

FIG. 1 illustrates, for example, extended portion 104 extending beyond the corresponding rear edge 72. It should be noted that the term "corresponding" is used to refer to a second component that is positioned similarly (to the first component) at the front or rear of the article 100 and thus identified with the same "front" or "rear" label, e.g., front edge 20a of the stretch panel 20 corresponds with front edge 71 of the absorbent assembly 10. The extension provided by portion 104 helps in fastening the front and rear waist portions 112, 110 of absorbent assembly 10 when the absorbent article 100 is worn by a user. In this respect, the portion 104 is referred to herein as a fastening portion 104, or more particularly, a rear fastening portion 104.

Furthermore, the stretch panel 20 is provided with fastening elements 31, 32 to further facilitate fastening and securing of the front and rear waist portions 112, 110. These fastening elements 31, 32 form a fastening system of the disposable absorbent article 100. During the manufacture of the stretch panel 20, zones or regions having substantially zero elasticity are created, for example, by intermittently applying an adhesive supply. In FIG. 1, these substantially inelastic zones provide a finger-lift area 31 and a landing area 32 upon which to apply a fastening element.

In the embodiment of FIGS. 1 and 2, the fastening system includes another fastening element 40 in the form of a hook fastener, such as that widely used in the art as part of hook and loop fastening systems. When the absorbent article 100 is worn, the fastening portions 104 loop about the thighs of the user and attaches to the front edge 20a of the stretch panel 20 via attachment of hook element 40 (see, e.g., FIGS. 6A-6B and FIG. 7). A nonwoven material used in the construction of the stretch panel 20 acts as the loop element of the fastening system. The hook element 40 is selected to ensure good compatibility with loops formed by the nonwoven material. In alternative embodiments, the article may utilize other known fastening systems, including fastening systems based on pressure sensitive adhesives and silicone release tapes.

Figure 3A:
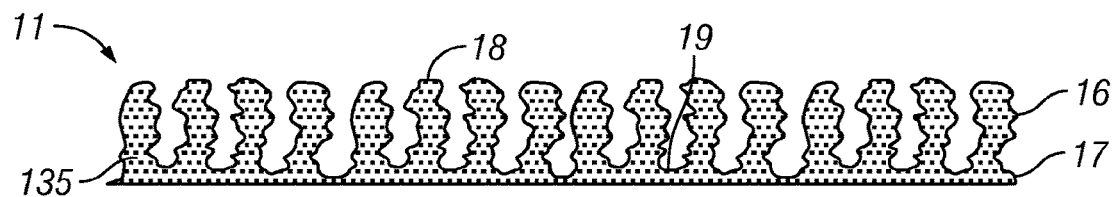
FIGS. 3A and 3B are cross-sectional and top views, respectively, of an embodiment of an absorbent core.
Figure 3B:
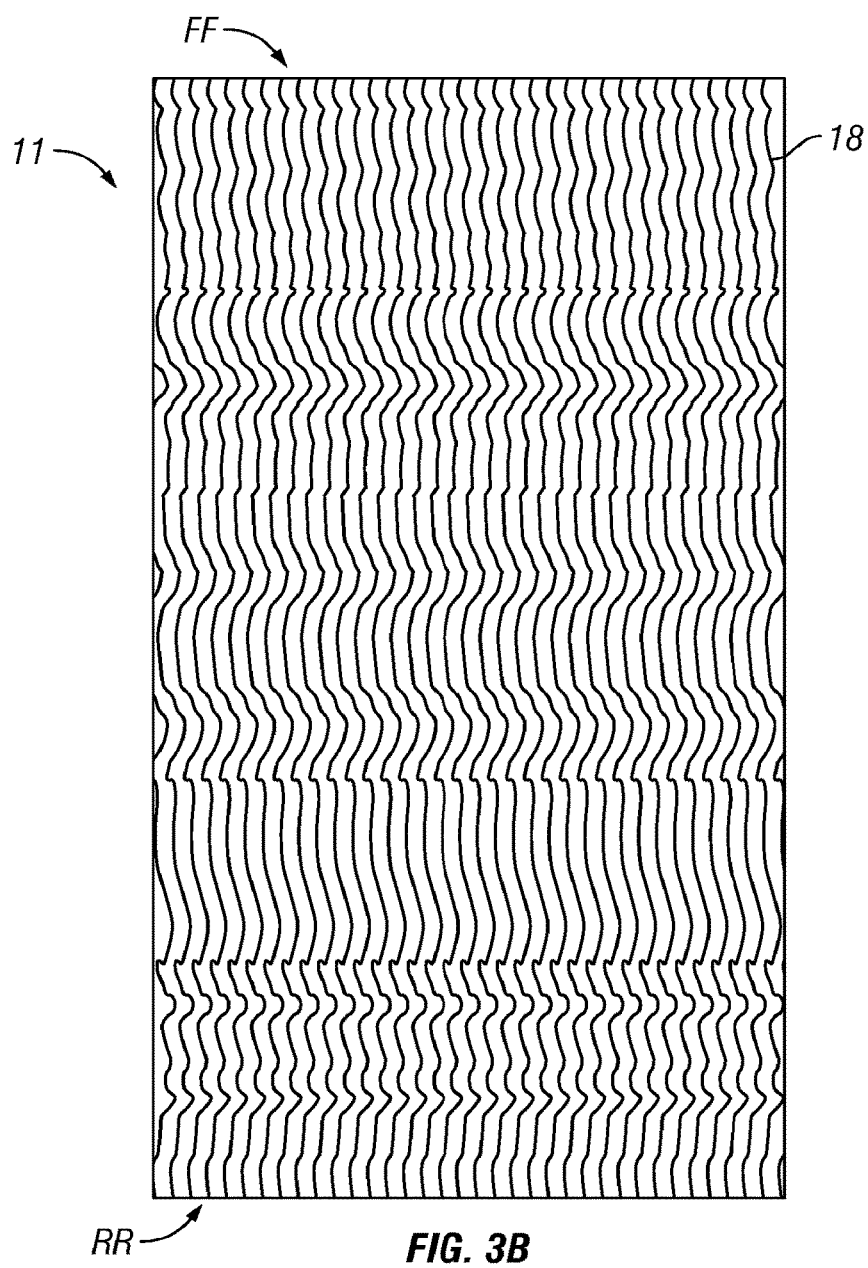

FIGS. 3A and 3B show a cross-section view and a top view of absorbent core 11. Absorbent core 11 comprises a riffled substrate 16 coupled to a flat substrate 17. Riffled substrate 16 comprises a plurality of peaks 18 and troughs 19 that run substantially along the length of absorbent core 11. In certain embodiments, this means peaks 18 and troughs 19 run in the machine direction of absorbent core 11. That is, while peaks 18 and troughs 19 may be irregular and may run toward the long edges of absorbent core 11 at specific locations, peaks 18 and troughs 19 generally run parallel to the long edges of absorbent core 11 and the longitudinal center line of the absorbent article.

Riffled substrate 16 has a total surface area greater than its footprint (that is, its gross length times its gross width). Flat substrate 17 has a total surface area substantially equal to its footprint. The surface area of riffled substrate 16 is greater than the surface area of flat substrate 17. In various embodiments, the surface area of riffled substrate 16 is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.8, 7.7, 7.8, 7.9, 8.0 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, or 18.0 times the surface area of flat substrate 17. In some embodiments, the surface area of riffled substrate 16 is more than 18.0 times the surface area of flat substrate 17.

In the illustrated embodiment, riffled substrate 16 and flat substrate 17 comprise tissue. In one embodiment, tension is applied to a substrate to create riffled substrate 16. The depth of the troughs 19 (and also consequently the height of the peaks 18) are correlated to the amount of tension applied to the substrate.

In the illustrated embodiment, flat substrate 17 is laminated to riffled substrate 16.

Other suitable substrates known in the art may be used in other embodiments: for example, riffled substrate 16 or flat substrate 17 may comprise nonwoven fabric.

Super absorbent polymer (SAP) 135 is disposed within absorbent core 11, between riffled substrate 16 and flat substrate 17. In various embodiments, SAP may comprise polyvinyl alcohol, polyacrylates, various grafted starches, and cross-linked sodium polyacrylate. In the illustrated embodiment, SAP is in the form of particles, but in other embodiments SAP may be in the form of fibers, foams, web, spheres, agglomerates of regular or irregular shapes, and film.

FIGS. 4A-4E depict one embodiment of a method for manufacturing absorbent core 11. First, riffled substrate 16 is dispensed. In one embodiment, riffled substrate 16 is dispensed from a roll. In another embodiment, a flat substrate may be treated (for example, by applying tension, by wetting, and/or by applying an adhesive) to form riffled substrate 16.

Figure 4A:
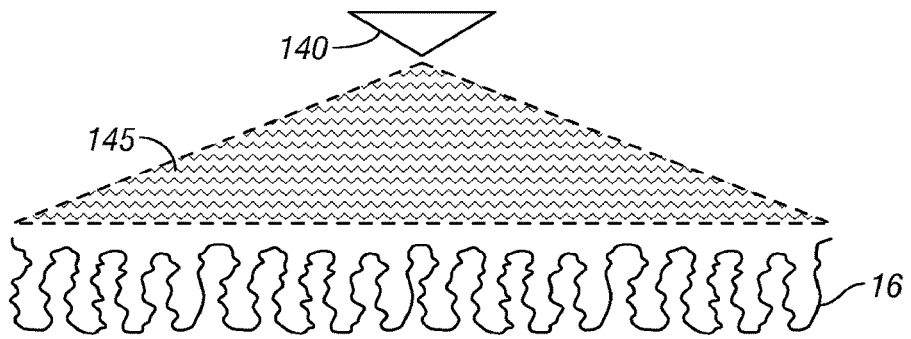
FIGS. 4A-4E are illustrations of an embodiment of a method of making an absorbent core.
Figure 4B:
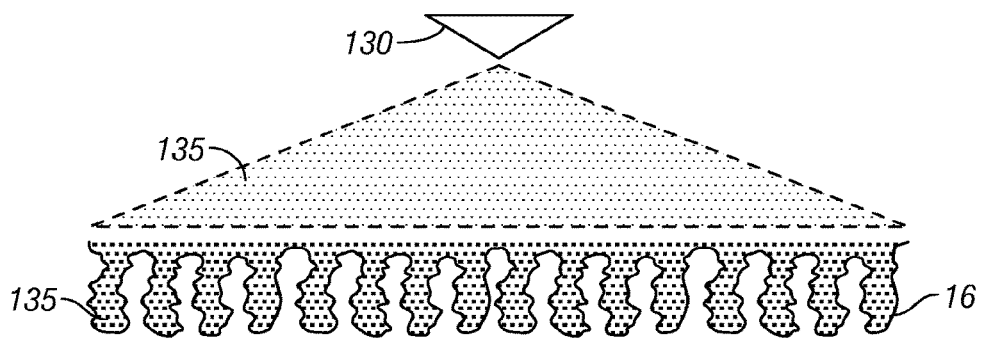

As shown in FIG. 4A, an adhesive dispenser 140 applies adhesive 145 to riffled substrate 16. Then, as shown in FIG. 4B, an SAP dispenser 130 then applies SAP 135 to riffled substrate 16. In another embodiment, the SAP may be applied first, and then the adhesive may be applied. In the embodiment shown, SAP 135 is located primarily within the valleys of riffled substrate 16.

In other embodiments, SAP 135 may be bound riffled substrate with a binder instead of adhesive 145.

Figure 4C:
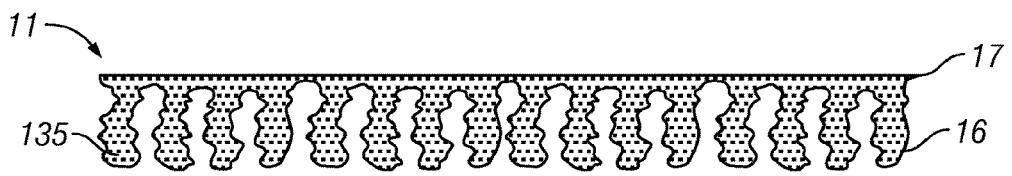

Once SAP 135 and adhesive 145 have been applied to riffled substrate 16, flat substrate 17 is coupled to riffled substrate 16 forming absorbent core 11, as shown in FIG. 4C. in the illustrated embodiment, flat substrate 17 is laminated to riffled substrate 16.

In other embodiments, SAP 135 may be applied to flat substrate 17 instead of or in addition to riffled substrate.

Figure 4D:
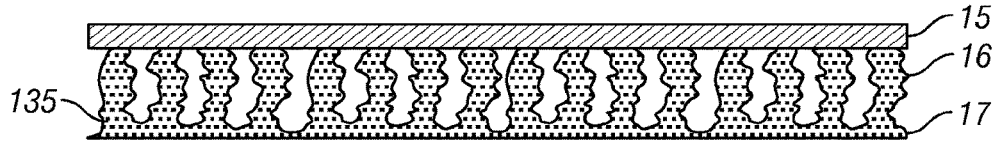
Figure 4E:
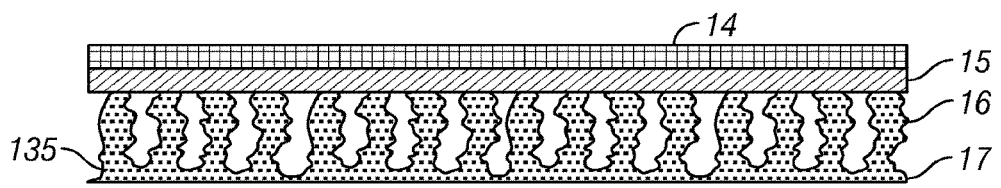

In various embodiments, additional layers may be applied to absorbent core 11. For example, as shown in FIG. 4D, a distribution layer 15 is coupled (e.g., laminated) to riffled substrate 16. As shown in FIG. 4E, an acquisition layer 14 may then be coupled (e.g., laminated) to distribution layer 15. In the illustrated embodiment, distribution layer 15 and acquisition layer 14 comprise curly-fiber airlaid. One example of suitable curly-fiber airlaid, V-Test 1309, is available from McAirlaid's Inc. USA, 180 Corporate Drive Rocky Mount Va. 24151.

Figure 5A:
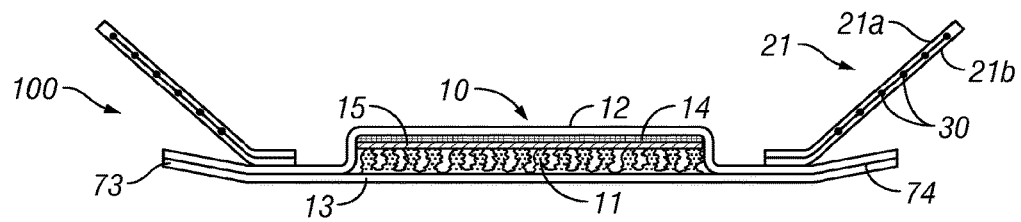
FIGS. 5A-5E are cross-sectional views across line 5-5 in FIGS. 1 and 2, illustrating various alternative embodiments of the invention.
Figure 5B:
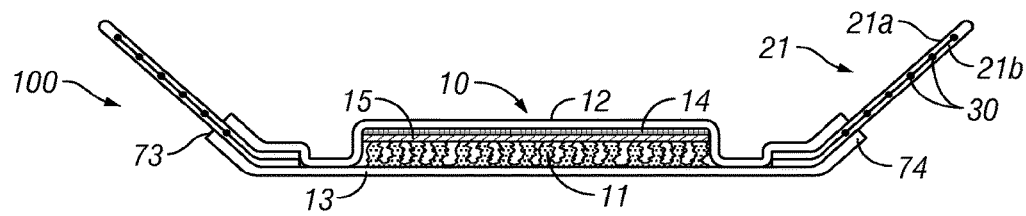
Figure 5C:
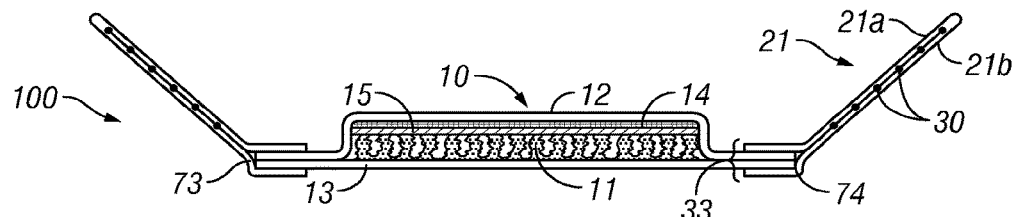
Figure 5D:
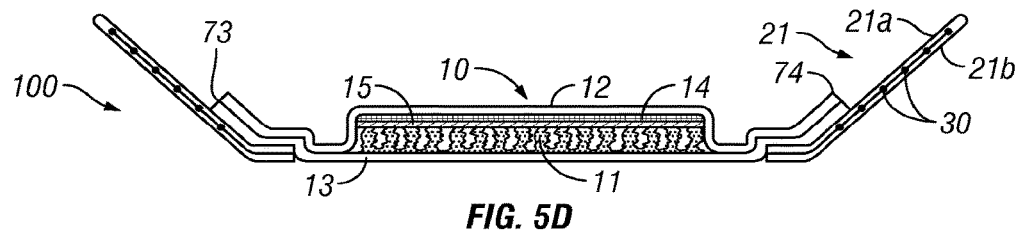

FIGS. 5A-5E are various cross-sectional views of embodiments of disposable absorbent article 100. Each of FIGS. 5A-5D illustrates a stretch panel 20 in the form of a separately attachable machine direction elongated stretchband 21. In FIG. 5A, stretchband 21 is attached to nonwoven topsheet 12. In the embodiment of FIG. 5B, stretchband 21 is attached between nonwoven topsheet 12 and backsheet 13. FIG. 5C provides another embodiment of the invention wherein the stretchband 20 includes a selvedge 33 that is attached to the upper surface of topsheet 12 and the lower surface of backsheet 13. In the embodiment of FIG. 5D, stretchband 21 is attached to backsheet 13. It should also be noted that the stretch panel 20 or stretchband 21 can be attached to the lateral edges of absorbent assembly 10 using any of the methods for assembling diaper components known to those skilled in the relevant art. Such methods may involve, for example, the use of hot melt adhesive and/or ultrasonic bonding.

Figure 5E:
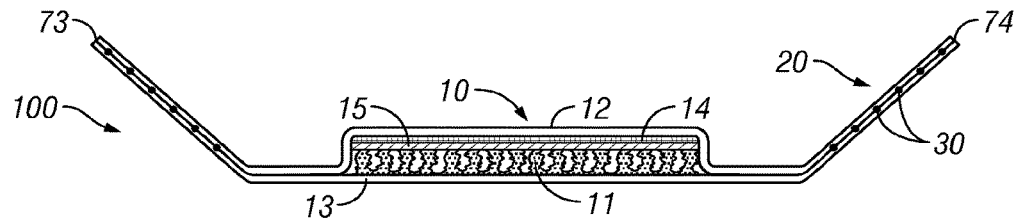

FIG. 5E depicts another embodiment of article 100 where lateral edges 73, 74 of the absorbent assembly 10 extend beyond the absorbent assembly 10 to form stretch panels 20. Elastomeric elements 30 are disposed between the topsheet 12 and backsheet 13 of absorbent assembly 10 to impart elasticity to the stretch panels 20. Unlike the embodiments shown in FIGS. 5A-5D, the stretch panels 20 of FIG. 5E are formed as a unitary part of the absorbent assembly 10 rather than separately from it.

Stretchband 21 is a material assembly that is preferably elasticized in the longitudinal, machine direction, but may also be elasticized in the lateral, cross direction. The material assembly includes a top layer 21a, a base or bottom material layer 21b, and a plurality of elastic elements 30 sandwiched between the top and bottom material layers 21a, 21b. In an alternative embodiment, stretchband 21 is formed using a single wide layer of nonwoven that is folded over the elastic elements. Typically, elastomeric elements 30 are elastomeric threads or strands which are pre-tensioned and then glued or otherwise adhered to top and bottom material layers 21a, 21b. Elastication may also be provided by other elasticizing means known to those skilled in the art, including solid elasticizing films, liquid applied elastomer, elastomeric ribbons, elastic foam, or rubber. The top and bottom material layers 21a, 21b may be provided by a polypropylene, nonwoven material, such as those often used to make the topsheet or leg cuff components of a conventional disposable diaper. Alternatively, one or both of top and bottom layers 21a, 21b may be provided by a polyethylene film or laminated nonwoven/film combination such as that used for the backsheet of a conventional disposable diaper. In stretch panel 20 of FIG. 5E, topsheet 12 and backsheet 13 provides the top and bottom material layers.

In a preferred embodiment, stretchband 21 is provided with several longitudinally-extending elastomeric threads or strands 30 which are sandwiched between top and bottom layers 21a, 21b, of a nonwoven fabric. The nonwoven fabric is preferably of a basis weight between about 10 and 100 grams per square meter. Using a hot-melt adhesive, the elastomeric strands 30 are applied to a web of the nonwoven fabric in an elongated pre-tensioned state (e.g., between about 50% and 500% elongation). When the stretchband web is later cut to form discrete stretchbands, elastomeric strands 30 are also cut and released from sections or regions near the ends of the stretchband 21. Now void of elastomeric material, these end regions become substantially de-elasticized or non-elasticized zones 31, 32. Zones 31, 32 then provide a finger-lift area 31 and a landing area 32 upon which to apply fastening elements.

Figure 8:
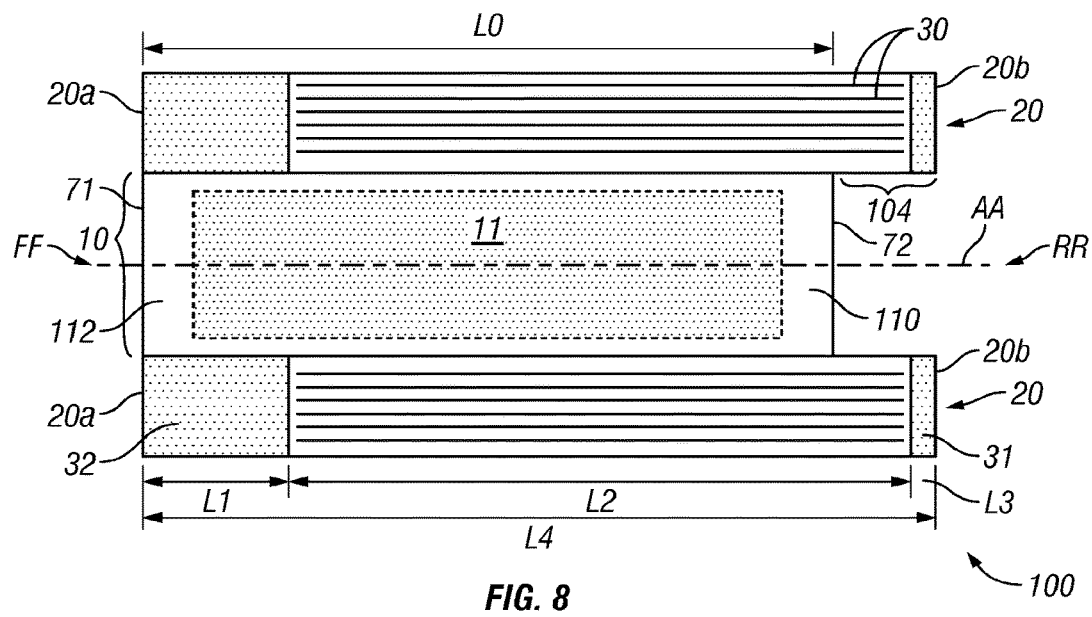
FIG. 8 is a plan view of the disposable absorbent article of FIG. 1, wherein various dimensions are highlighted.
Figure 9:
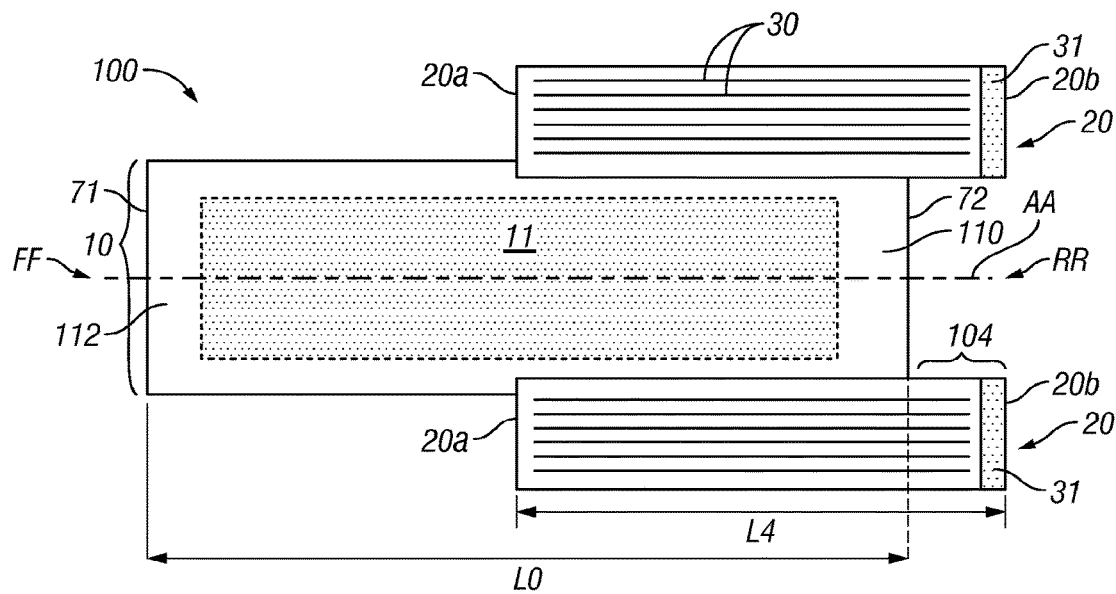
FIG. 9 is a plan view of yet another alternative embodiment of the inventive disposable absorbent article.
Figure 10A:
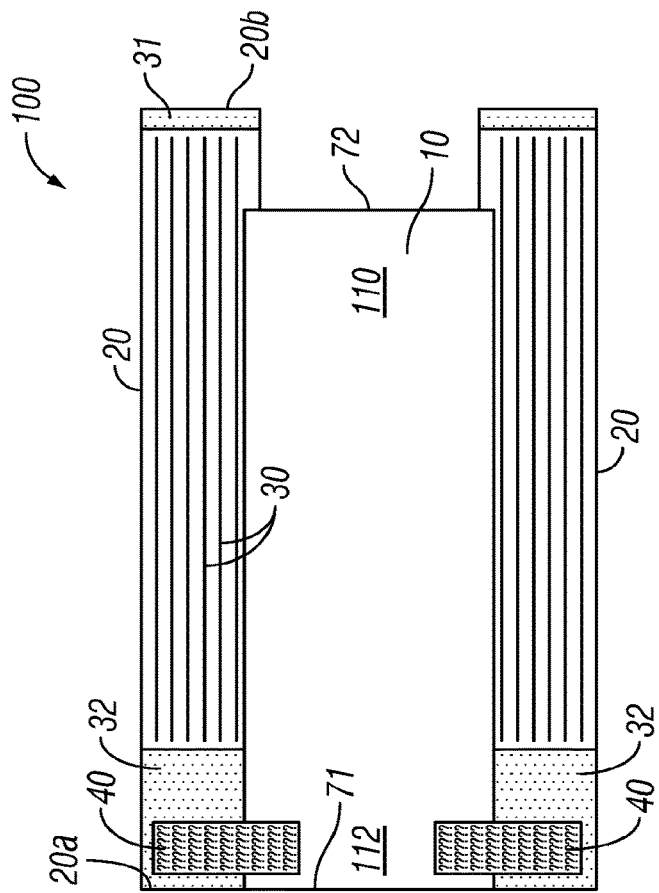
FIGS. 10A-10D are plan views of alternative embodiments of the invention incorporating various fastening elements.
Figure 10B:
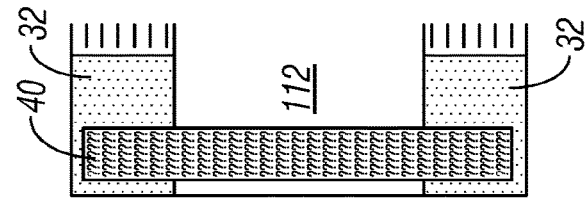
Figure 10C:
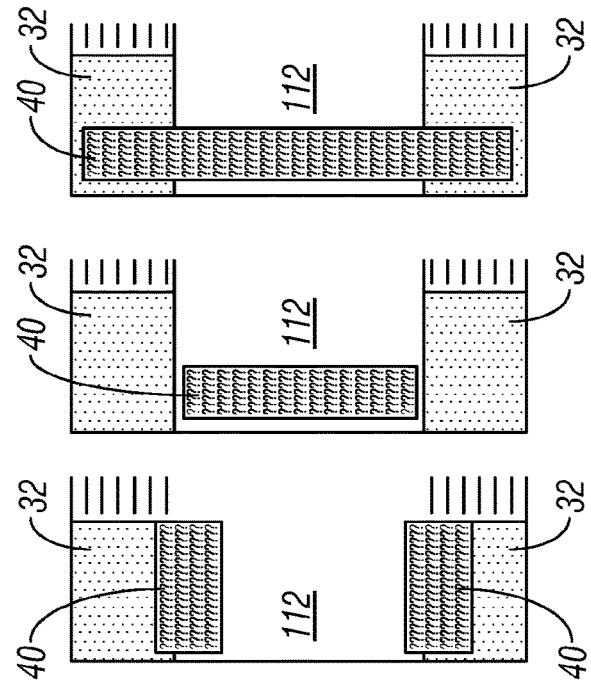
Figure 10D:
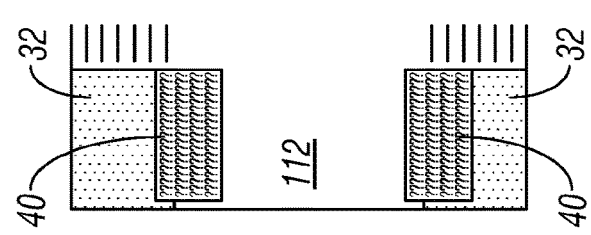

In an alternative embodiment of the invention as illustrated by FIG. 8, the total length L4 of the stretch panel 20 is less than the length L0 of absorbent assembly 10. Stretch panel 20 is again positioned, however, to overlap and extend beyond the rear longitudinal edge 72 of absorbent assembly 10, thereby providing fastening portion 104. Specifically, front edge 20a of stretch panel 20 is positioned between front edge 71 and rear edge 72 of the absorbent assembly 10. In this embodiment, the total length L4 of stretch panel 20 is preferably between about 0.5 to 1.0 times the length L0 of absorbent assembly 10.

Figure 6A:
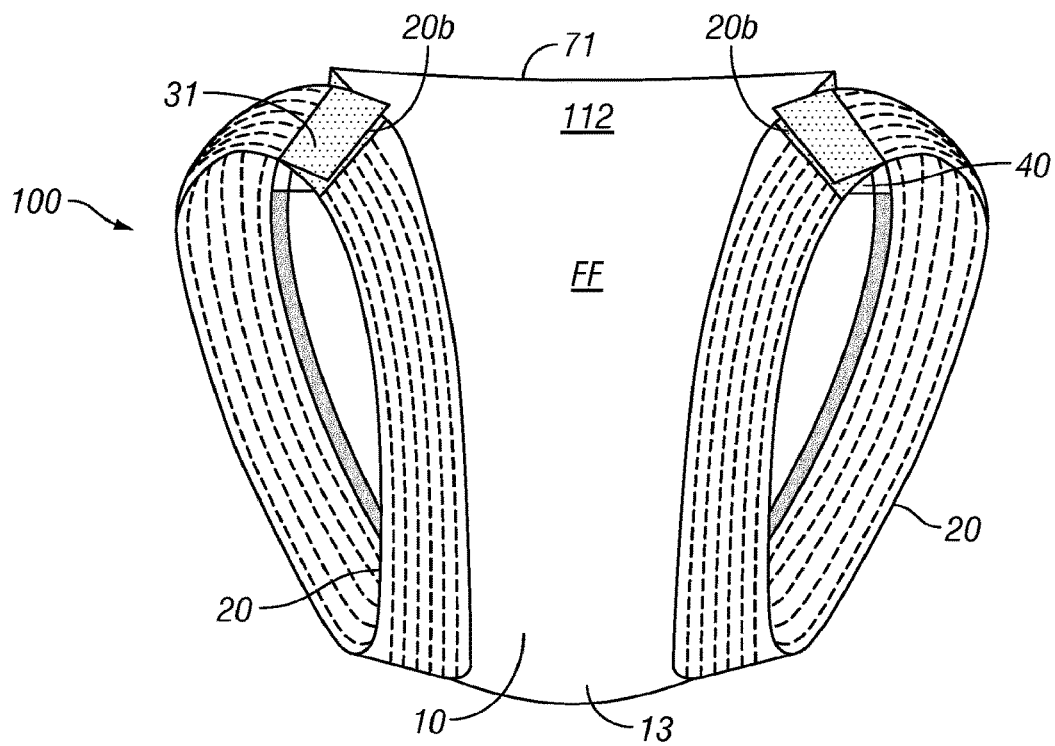
FIGS. 6A and 6B are front and side views, respectively, of the disposable absorbent article of FIG. 1 as it would appear worn by a user.
Figure 6B:
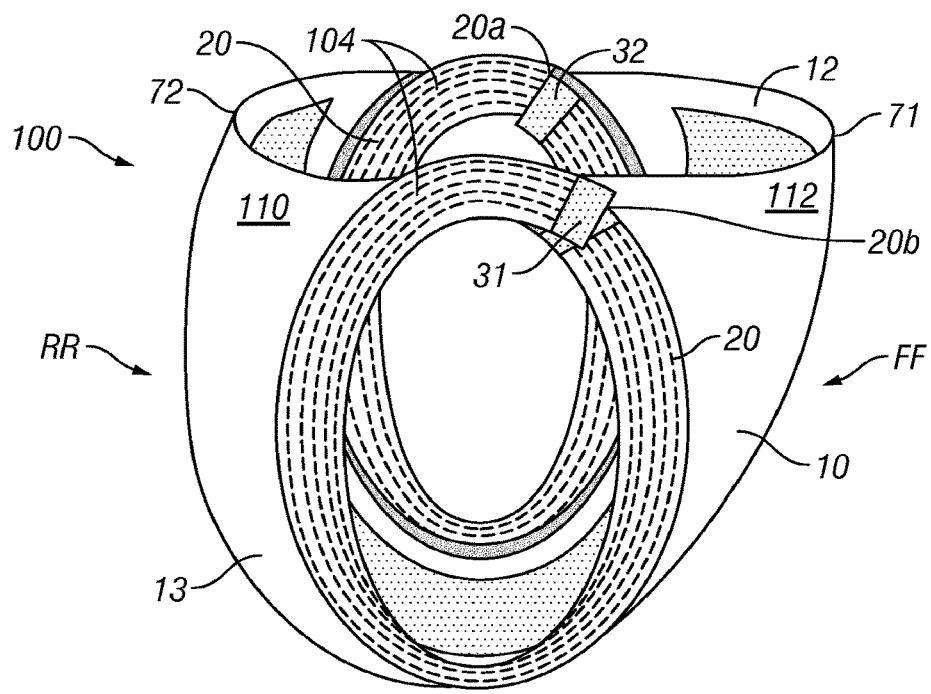
Figure 7:
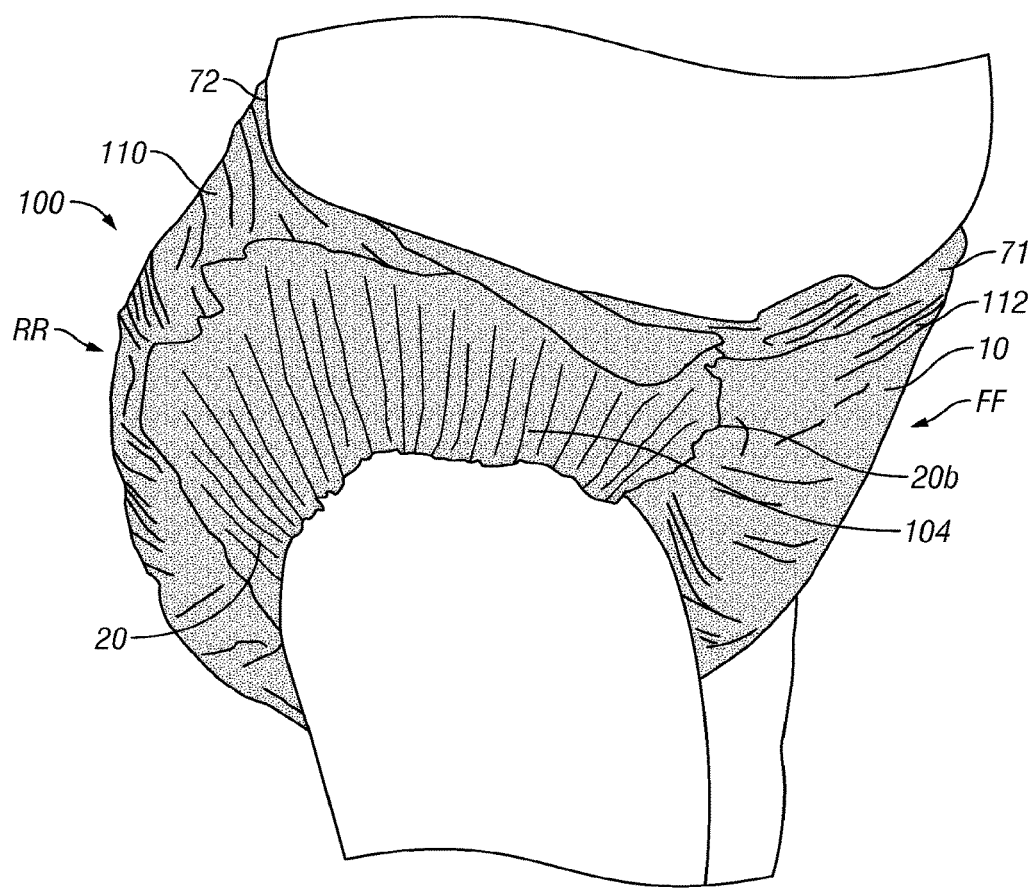
FIG. 7 is an alternative side view of the disposable absorbent article of FIG. 1, as it would appear when worn by a user.

FIGS. 6A and 6B depict front and side views of article 100 as it would appear when worn by a user. Stretch panels 20 are looped around the thighs of the user such that front and rear edges 20a, 20b mutually engage. In this way, front and rear waist portions 112, 110 are fastened together, thereby forming an all-around waist portion about the user. It should be noted that the front and rear waist portions 112, 110, or more particularly, front and rear edges 71, 72 of absorbent assembly 10 do not have to actually contact each other when fastened (see e.g., FIGS. 4 and 5). More importantly, stretch panels 20 allow for front and rear waist portions 112, 110 to encircle the waist of the user as shown in FIG. 5. Portions 104 add or extend front and rear waist portions 112, 110 to form a continuous waist portion encircling the user. This illustrates one way that fastening portion 104, and thus, stretch panels 20, facilitates the mutual attachment of the front and rear waist portions 112, 110.

FIG. 8 is a reproduction of FIG. 1 that highlights certain important dimensions of the inventive disposable absorbent article 100. In this embodiment of the invention, the overall extended length L4 of the stretch panel 20 is equal to the lengths L1 and L3 of the substantially non-elastic zones plus the length L2 of the elasticized zone. Preferably, the length L1 of the front non-elasticized zone is no less than about 5% and no greater than about 60% of the total length L4 of stretch panel 20. As shown in the figures, the total length L4 of stretch panel 20 exceeds the length L0 of absorbent assembly 10. Further, stretch panel 20 is positioned to overlap and extend beyond rear longitudinal edge 72 of absorbent assembly 10, thereby providing extended fastening portion 104. In this embodiment, the ratio of the total length L4 of the stretch panel 20 to the length L0 of absorbent assembly 10 is greater than about 1.05 and less than about 1.50.

The disposable absorbent article according to the present invention provides a close fitting seal around the thighs of the user, thereby significantly improving its leakage prevention capability. Referring now to FIGS. 10A-10D, the close fitting seal of the inventive garment 100 is further enhanced through addition of a fastening element 40 near the front edge 20a of the stretch panel 20. The fastening element 40 is preferably provided by at least one hook fastening device 40 constructed of extruded hooks or mushroom-shaped hooks. More preferably, the hook fastening element 40 is selected so as to be engageable with the microscopic loops formed on the surface of a nonwoven fabric. Thus, the nonwoven material of the stretchband panel provides the loop element of a hook and loop fastening system similar to those generally known in the art.

FIGS. 10A-10D provide various possible arrangements of hook fastening element 40 along front edge 20a of stretch panel 20. In the first embodiment of FIG. 8A, two laterally extending patches of hook fastening element 40 is provided near front edge 20a of each stretch panel 20. In the embodiment of FIG. 8B, hook fastening element 40 is a single patch that extends across front waist region 112 of absorbent assembly 10 and into non-elasticized zones 32 of stretch panels 20. In FIG. 8C, hook fastening element 40 is again a single patch that extends across front waist region 112 but not over non-elasticized zones 32. The embodiment of FIG. 8D is similar to that of FIG. 8A, except that the patch of hook fastening element 40 extends longitudinally rather than laterally.

In further embodiments, a loop landing tape may be located near the front waist region 112 of the outside face of the inventive article 100, and a pair of hook fastening elements may be located in the rear non-elasticized zones 32 of each stretch panel 20. The fastening portion 104 is, therefore, attached directly to the central body 10 rather than to the front edge 20a of the stretch panel 20. The loop landing tape may be constructed from a knitted, extruded, or non-woven material, as is generally known in the art.

It is important that the tension forces provided by the stretch panel 20 are neither too low nor too high. If the tension forces geed by the stretch panel 20 are too low, the absorbent article 100 may not fit very closely in certain regions around the legs and the waist and the absorbent article ability to prevent leakage will be compromised. High tension forces may constrict the user's thighs and cause discomfort. In a typical prior art disposable absorbent article, the positioning of elastomeric elements (and the type of elastomeric element placed) does not vary along the length of the stretch panel. The elasticity or elastication of the stretch panel is, therefore, uniform along the stretch panel length. When elongated in a uniform manner, the overall tension provided by the stretch panel is also uniform along its length. The magnitude of this uniform tension depends on the overall elongation of the stretch panel. When the absorbent article is worn, however, the elongation of the stretch panel along it length is generally non-uniform, and thus, the tension generated varies. As a result, there may be regions about the length of the stretch panel that are undesirably too loose or too tight.

In accordance with a preferred embodiment of the invention, a disposable absorbent article, or more precisely, a stretch panel, is provided wherein the elasticity and the tension forces generated along the longitudinal length of the stretch panel vary in a predetermined manner. Applicants have discovered that certain predetermined, non-uniform distributions of elastic elements impart a desirable variance in elasticity along the length of the stretch panel. This variance in elasticity provides a desirable tension gradient when the disposable absorbent article is worn by the user. In a further aspect of the present invention, Applicants have also discovered that, by providing certain regions or zones along the length of the stretch panel with a distinct elasticity (imparted by the elastic elements) the fit and sealing capabilities of the absorbent article may be enhanced.

Thus, in one aspect of the invention, the number, type, and/or application of elastomeric strands 30 are varied along the length of the stretch panel 20 such that the elasticity imparted by the elastomeric strands along the stretch panel length also varies. As a result, distinct regions or zones of elasticity are created in the vicinity of the elastomeric strands and along the stretch panel length. The relative elasticity of these distinct regions are generally predetermined to effect a desired tension gradient about the stretch panel when the disposable absorbent article is worn (further discussed below).

In one respect, regions or zones devoid of elastic elements—e.g., zones provided for finger lift area 31 and landing area 32—are also distinct regions of elasticity formed by pre-determined placement of elastic elements. These regions of elasticity differ, however, in the sense that the elastic elements 30 do not impart elasticity to the stretch panel 20 in these regions (in contrast to the distinct regions of imparted elasticity in the vicinity of the elastic elements).

Figure 11:
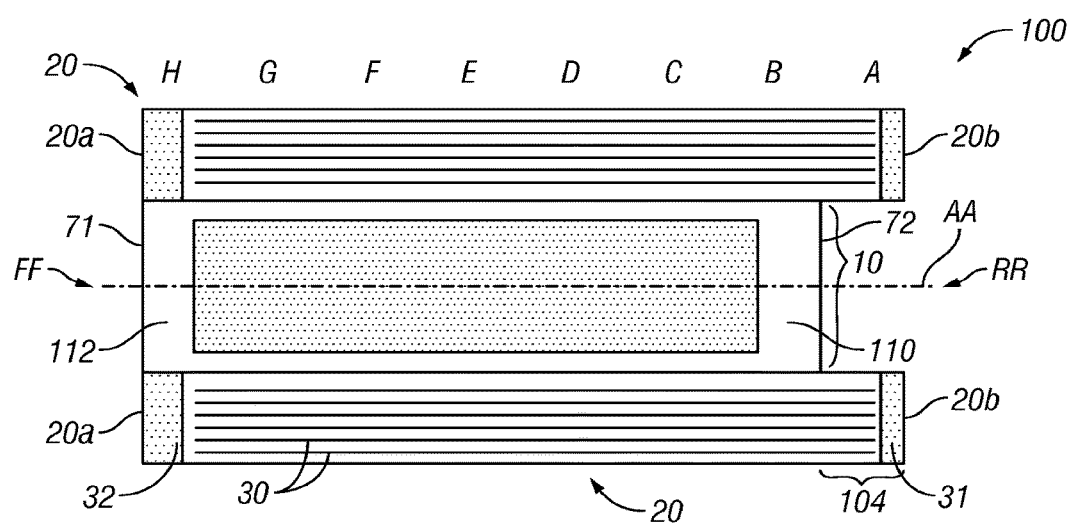
FIG. 11 is a plan view of a first embodiment of the invention, with regions of the stretch panel labeled.
Figure 12:
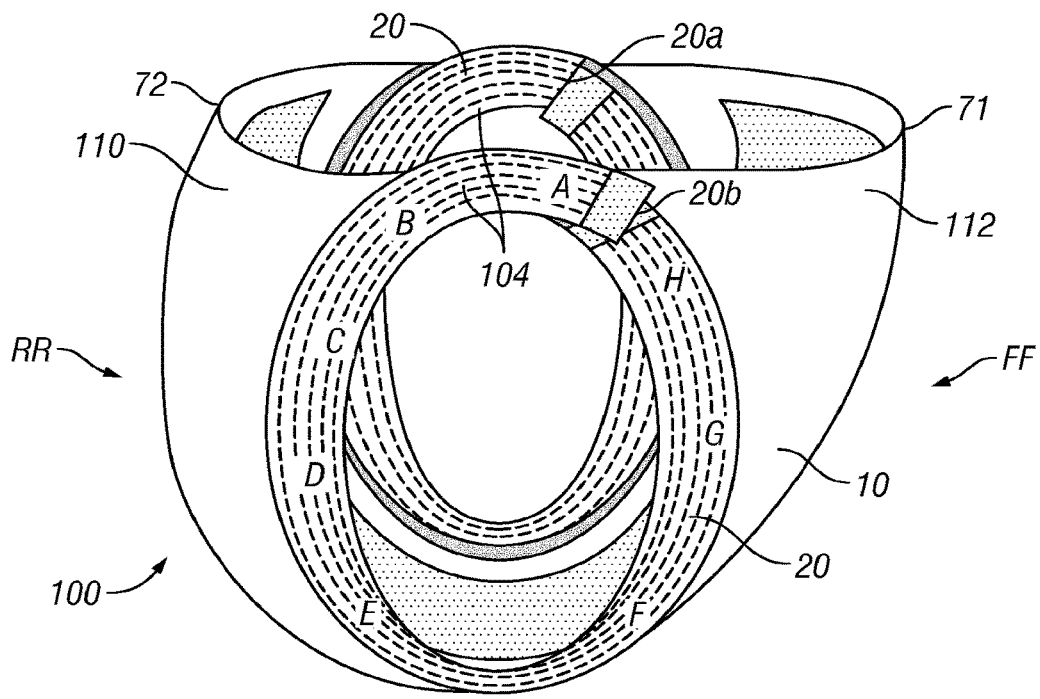
FIG. 12 is a side view of the first embodiment of the inventive disposable absorbent article as it would appear worn by a user and with the stretch panel labeled in correspondence with the plan view of FIG. 11 and the graphical illustration of FIG. 13.

To facilitate the present discussion, FIGS. 11 and 12 provide two views of a disposable absorbent article 100 according to one embodiment of the invention, wherein regions or zones along the longitudinal length of the stretch panel 20 are indicated alphabetically. FIG. 11 provides a view of the disposable absorbent article 100 in a generally flat, open condition. FIG. 12 provides a side view of the disposable absorbent article 100 as it would appear worn by a user, wherein the regions or zones are marked about the stretch panel 20. In both views, the longitudinal length of the stretch panel 20 is marked by reference letters A-H, with A referring to the region or zone nearest the rear edge 20b and reference letter H referring to the region or zone nearest the front edge 20a. The chart of FIG. 13 corresponds with FIG. 12 and indicates the tension provided along the length or loop of the stretch panel 20 in the various regions A-H, when the article is worn by a user.

Figure 13:
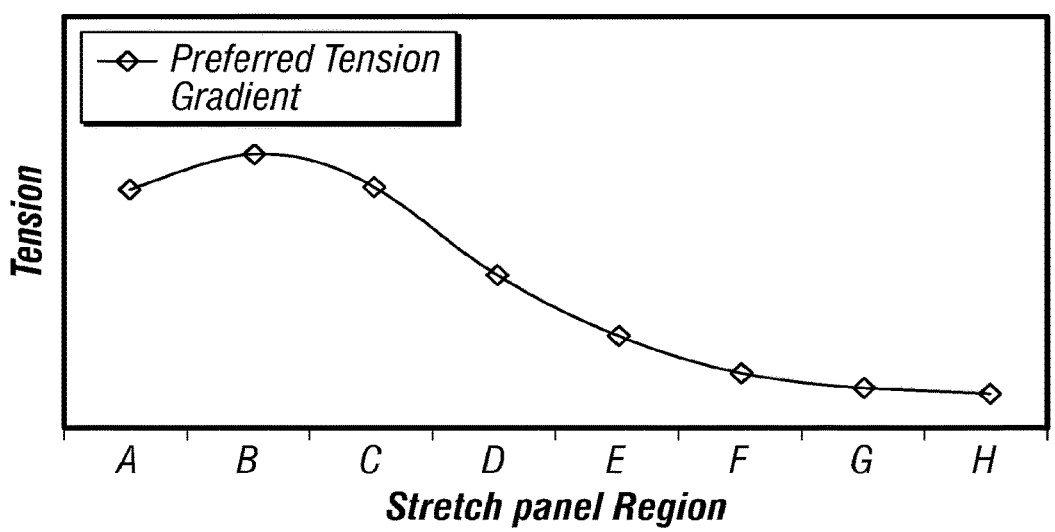
FIG. 13 is a graphical illustration of a tension gradient corresponding with the labeled regions of the stretch panel in FIG. 11.

As illustrated by the chart of FIG. 13, the tension generated by the stretch panel 20 when the article 100 is worn varies advantageously in a pre-determined manner. This variance in tension or tension gradient is obtained by designing the stretch panel 20 so as to have distinct elastic properties along its length. More specifically, distinct regions of elastication are provided by selecting or designing certain characteristics (e.g., pre-tensioning, quantity, concentration, type, etc.) of the elastomeric elements 30 in the various regions, thereby obtaining the desired tension gradient. Preferably, the stretch panel 20 is designed such that a region(s) near the rear edge 20b (i.e., region B) has the greatest elasticity and a region(s) near the front edge 20a has the lowest elasticity (i.e., region G). Referring to FIG. 13, the combination of the elastic properties of the stretch panel 20 and elongation of the stretch panel 20 when the article 100 is worn, provide a region of maximum tension around region B and a region of minimum tension around region H. It should be noted that the embodiments of FIGS. 11 and 12 utilize one size and type of elastic elements. In alternative embodiments, the type, size, and number of elastic elements may be varied along the stretch panel length.

Figure 14:
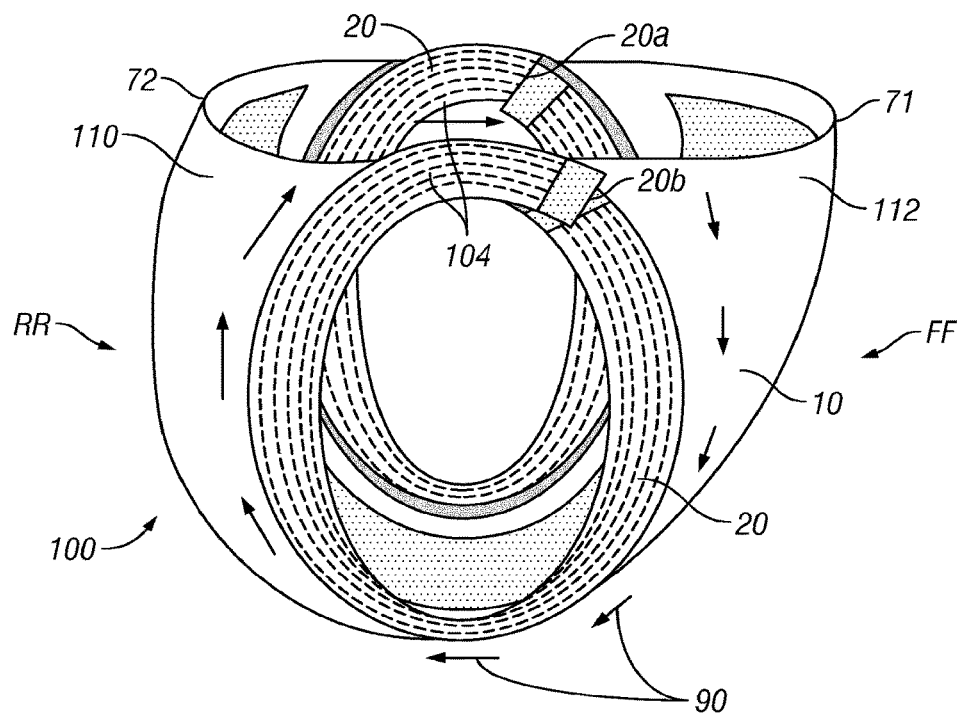
FIG. 14 is a side view of a disposable absorbent article according to the present invention as it would appear worn by a user and with the magnitude of tension forces along the length of the stretch panel represented.

Preferably, the elasticity and thus the tension associated with the various distinct regions of the stretch panel 20 increases in the direction from the front edge 20a to the rear edge 20b. Referring to FIG. 13, elasticity of the stretch panel 20 is at a maximum in region B, which is in the vicinity of the rear longitudinal edge 20b and adjacent rear edge 72 and rear waist portion 110 of the absorbent assembly 10. Together, regions A, B and C provide regions of the greatest elasticity along the longitudinal length of the stretch panel 20. On the other hand, region H, which is closest to the front edge 20a of the stretch panel 20 and closest to the front waist portion 112 of the absorbent assembly 10, provides a region of minimum elasticity. Accordingly, in a preferred embodiment of the invention, the stretch panel 20 is characterized by tension forces which are significantly greater around the waist and down the back of the thigh of the user, than corresponding regions at the front FF of the disposable absorbent article 100. FIG. 14 provides a side view illustration of a disposable absorbent article 100 as worn by a user. In this figure, the size of the arrows 90 indicate the magnitude of the tension forces in that region of the stretch panel 20. As clearly shown therein, the tension forces of the stretch panel 20 increases in the direction from the front edge 20a to the rear edge 20b. One desirable effect of this tension gradient is that the tension generated in the rear portions of the stretch panel 20 (especially in regions A-D) pulls the waist portion 112 toward the user and enhances the seal between the front edge 71 and the user's waist.

Figure 15:
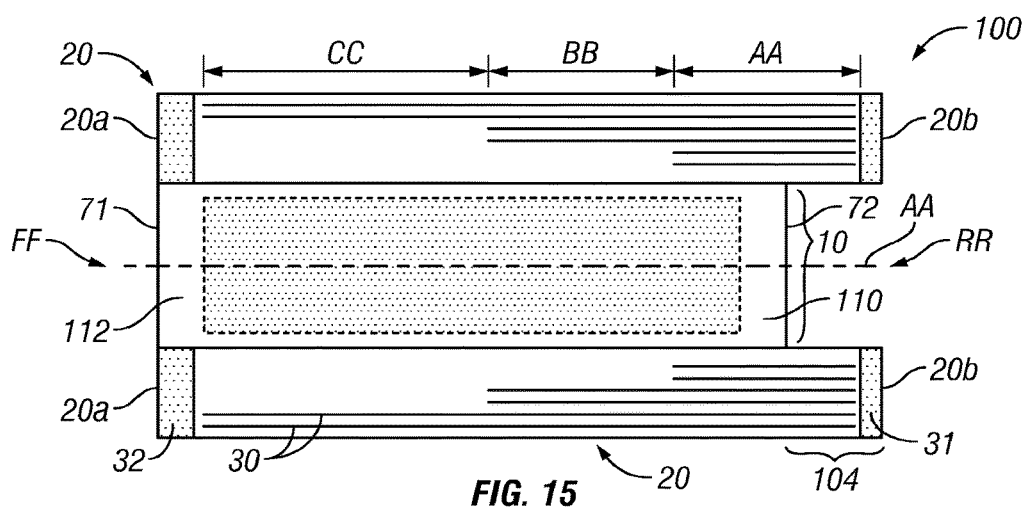
FIG. 15 is a plan view of another alternative embodiment of the invention utilizing varying lengths of elastic strands.

The elastomeric elements may be varied in types, size, concentration, arrangement, and/or application (to the stretch panel) so as to achieve the desired variance in the elasticity imparted by the elastomeric elements to various regions of the stretch panel. FIG. 15 illustrates one method of achieving such variance.

In the embodiment of FIG. 15, the number of elastomeric strands 30 secured within the stretch panel 20 increases in the direction from the front edge 20a to the rear edge 20b. In region CC (near the front edge 20a), the stretch panel 20 has two elastomeric strands, while in regions BB and AA (near the rear edge 20b), the stretch panel has four and six strands, respectively. Thus, the elasticity imparted on the stretch panel 20 is lowest in the vicinity of the front edge 20a and greatest in the vicinity of the rear edge 20b. Accordingly, the tension generated in the stretch panel 20, when the article 100 is worn, is at a minimum at region CC and at a maximum at region AA.

The stretch panel depicted in FIG. 8 provides a tension gradient similar to that associated with the embodiment of FIG. 15 when the absorbent article 100 is worn by a user. Referring to FIG. 8, the front region or non-elastic zone 32 is void of any elastic elements, and thus, the absorbent article 100 provides a region of minimum elasticity and tension forces near the front edge 20a. Conversely, the stretch panel 20 provides a region of higher elasticity and tension forces near the rear edge 20b. Alternatively, by increasing the area of the non-elasticized zone 32 near the rear edge 20b and decreasing the area of the non-elasticized zone 32 near the front edge, the elasticity and tension forces of the stretch panel 20 will be higher in the front region than in the rear region. The tension gradient generated by such a configuration will be generally the reverse of that represented in FIG. 13.

It should be noted that the preferred embodiment is one wherein the elasticity of the stretch panel generally increases in the direction from the front edge 20a to the rear edge 20a, and wherein the region of maximum of elasticity is provided near the rear edge 20a. As mentioned above, the higher elasticity near the rear edge 20a and along the rear of the disposable garment 100, as shown in FIG. 14, tends to pull the front waist region 112 of the disposable garment 100 towards the waist and body of the user, thereby providing for a closer fit and seal along the front waist region 112. In other embodiments, different arrangements or distributions of elasticity along the length of the stretch panel 20 may be employed to effect a different tension gradient and to address different sealing and comfort concerns.

It is considered that any combination of progressively increasing the lengths of the elastomeric threads and removal of elasticity at the front of the diaper may be used to provide the preferred elastic tension gradient represented in FIG. 13.

The claims are not to be interpreted as including means-plus- or step-plus-function limitations, unless such a limitation is explicitly recited in a given claim using the phrase(s) "means for" or "step for," respectively.

The invention claimed is:

1. A disposable absorbent article disposed in a generally flat, open condition, the disposable absorbent article comprising:
a central body including an absorbent core, a front longitudinal edge, and a rear longitudinal edge opposite said front longitudinal edge, wherein said front and rear edges of said central body define, at least partially, front and rear waist portions respectively and said central body is characterized by a longitudinal centerline extending across said front and rear edges; and
wherein the absorbent core comprises:
a riffled substrate comprising a plurality of peaks and a plurality of troughs;
a flat substrate coupled to the riffled substrate; and
superabsorbent polymer disposed between the riffled substrate and the flat substrate;
wherein the footprint of the riffled substrate is substantially the same as the footprint of the flat substrate; and
wherein the surface area of the riffled substrate is greater than the surface area of the flat substrate; and
wherein the peaks and troughs of the riffled substrate are spaced apart from the flat substrate.

2. The disposable absorbent article of claim 1, where the superabsorbent polymer is adhered to at least one of the riffled substrate or the flat substrate with an adhesive.

3. The disposable absorbent article of claim 1, where the superabsorbent polymer is bound to at least one of the riffled substrate or the flat substrate with a binder.

4. The disposable absorbent article of claim 1, further comprising an acquisition layer coupled to the absorbent core.

5. The disposable absorbent article of claim 4, further comprising a distribution layer coupled to and between the acquisition layer and the absorbent core.

6. The disposable absorbent article of claim 5, wherein the riffled substrate is laminated to the flat substrate; wherein the distribution layer is laminated to the riffled substrate, opposite the flat substrate; and wherein the acquisition layer is laminated to the distribution layer opposite the riffled substrate.

7. The disposable absorbent article of claim 1, where the riffled substrate comprises tissue.

8. The disposable absorbent article of claim 7, where the flat substrate comprises tissue.

9. The disposable absorbent article of claim 1, where the riffled substrate comprises nonwoven fabric.

10. The disposable absorbent article of claim 9, where the flat substrate comprises nonwoven fabric.

11. The disposable absorbent article of claim 1, further comprising:
a pair of elasticized side panels distinct from said central body and extending longitudinally and adjacent opposite longitudinal sides of said central body a length sufficient to wrap around the legs of a user of the disposable absorbent article when worn, each said side panel having a front latitudinal edge, a rear latitudinal edge opposite said front latitudinal edge, a proximal longitudinal periphery edge, a portion of which is at least co-extensive with said central body, a distal longitudinal periphery edge, and at least one fastening portion for fastening said front and rear waist portions of said central body when the disposable absorbent article is worn by a user;
wherein the distal longitudinal periphery edge of the side panels are generally parallel to one another along the length of the side panels;
wherein each elasticized side panel comprises an elastic element, the elastic element providing a direction of stretch to said side panel that is generally parallel to said longitudinal centerline;
wherein said elastic element extends longitudinally past a corresponding said front or rear latitudinal edges of said central body, wherein said front latitudinal edge of said side panel is positioned closer to said front waist portion of said central body than to said rear waist portion of said central body;
wherein each said side panel includes a front or rear fastening portion formed by said side panel extending longitudinally past a corresponding said front or rear latitudinal edges of said central body, said front or rear fastening portion being constructed for fastening said front and rear waist portions of said central body when the disposable absorbent article is worn by a user; wherein each said fastening portion includes a first fastening element adapted to engage a second fastening element on said central body, wherein the first fastening element is located within the fastening portion and is longitudinally positioned past the latitudinal front or rear edge of said central body such that the fastening element is within the fastening portion in a section thereof which is not coextensive with the central body, and wherein said fastening element is in longitudinal alignment with an elasticized side panel;
wherein when the absorbent article is disposed in a relaxed, open and generally flat condition said central body, elasticized side panels and fastening portions all occupy a single plane;
wherein the fastening portions are integral to or permanently affixed to the disposable absorbent article;
wherein the elastic elements of said side panels disposed along said length of said side panel to impart elasticity therealong in a longitudinal direction sufficient to cause said side panels to engage the legs of the user when the disposable article is worn; and
wherein the amount of said imparted elasticity generally increases from the front to the rear of the legs, said increase in elasticity configured to provide tension at least around said front waist portion when worn.

12. The disposable absorbent article of claim 11, wherein said the elastic elements disposed along said length of said side panel impart elasticity therealong in the form a gradient of varying tension along the said portion of said length that is wrapped about the legs of a user when said disposable absorbent article is worn.

13. The disposable absorbent article of claim 11, wherein said elastic elements are positioned such that the elasticity of said side panel generally increases in the direction from said front edge of said side panel to said rear edge of said side panel.

14. The disposable absorbent article of claim 1, wherein said plurality of peaks are non-uniform.

15. The disposable absorbent article of claim 1, wherein each of said plurality of peaks extends in a non-linear manner between said front longitudinal edge and said rear longitudinal edge.

16. The disposable absorbent article of claim 1, wherein the superabsorbent polymer is in a form comprising particles.

17. The disposable absorbent article of claim 1, further comprising a distribution layer coupled to the riffled substrate, wherein voids are formed between the distribution layer and the riffled substrate.

18. The article of claim 1, wherein at least some of the superabsorbent polymer is disposed within space between troughs of the riffled substrate and the flat substrate.

19. The article of claim 1, wherein at least some of the superabsorbent polymer is disposed within space between peaks of the riffled substrate and the flat substrate.

20. The article of claim 1, wherein said article has a machine direction corresponding to a direction extending through said front and rear longitudinal edges, and wherein each of said peaks and troughs run in the machine direction or toward said front and rear longitudinal edges.

21. The article of claim 1, wherein the surface area of the riffled substrate is at least 18 times greater than the surface area of the flat substrate.

22. An absorbent core comprising:
a riffled substrate comprising a plurality of peaks and a plurality of troughs;
a flat substrate coupled to the riffled substrate; and
superabsorbent polymer disposed between the riffled substrate and the flat substrate;
wherein the footprint of the riffled substrate is substantially the same as the footprint of the flat substrate; and
wherein the surface area of the riffled substrate is greater than the surface area of the flat substrate; wherein the surface area of the riffled substrate is at least 18 times greater than the surface area of the flat substrate.

23. A disposable absorbent article disposed in a generally flat, open condition, the disposable absorbent article comprising:
a central body including an absorbent core, a front longitudinal edge, and a rear longitudinal edge opposite said front longitudinal edge, wherein said front and rear edges of said central body define, at least partially, front and rear waist portions respectively and said central body is characterized by a longitudinal centerline extending across said front and rear edges; and
wherein the absorbent core comprises:
a riffled substrate comprising a plurality of peaks and a plurality of troughs;
a flat substrate coupled to the riffled substrate; and
superabsorbent polymer disposed between the riffled substrate and the flat substrate;
wherein the footprint of the riffled substrate is substantially the same as the footprint of the flat substrate; and
wherein the surface area of the riffled substrate is greater than the surface area of the flat substrate;
further comprising an acquisition layer coupled to the absorbent core and a distribution layer coupled to and between the acquisition layer and the absorbent core; and
wherein the riffled substrate is laminated to the flat substrate; wherein the distribution layer is laminated to the riffled substrate, opposite the flat substrate; and wherein the acquisition layer is laminated to the distribution layer opposite the riffled substrate.

24. The disposable absorbent article of claim 23, wherein at least some of the superabsorbent polymer is disposed within space between troughs of the riffled substrate and the flat substrate.

25. The disposable absorbent article of claim 23, wherein the riffled substrate comprises tissue.

26. The disposable absorbent article of claim 23, wherein the distribution layer is coupled to the riffled substrate, and wherein voids are formed between the distribution layer and the riffled substrate.

27. A disposable absorbent article disposed in a generally flat, open condition, the disposable absorbent article comprising:
a central body including an absorbent core, a front longitudinal edge, and a rear longitudinal edge opposite said front longitudinal edge, wherein said front and rear edges of said central body define, at least partially, front and rear waist portions respectively and said central body is characterized by a longitudinal centerline extending across said front and rear edges; and
wherein the absorbent core comprises:
a riffled substrate comprising a plurality of peaks and a plurality of troughs;
a flat substrate coupled to the riffled substrate; and
superabsorbent polymer disposed between the riffled substrate and the flat substrate;
wherein the footprint of the riffled substrate is substantially the same as the footprint of the flat substrate; and
wherein the surface area of the riffled substrate is greater than the surface area of the flat substrate; and
wherein at least some of the superabsorbent polymer is disposed within space between troughs of the riffled substrate and the flat substrate.

28. The disposable absorbent article of claim 27, wherein the superabsorbent polymer is adhered to at least one of the riffled substrate or the flat substrate with an adhesive.

29. The disposable absorbent article of claim 27, where the riffled substrate comprises tissue.

30. The disposable absorbent article of claim 27, further comprising a distribution layer coupled to the riffled substrate, wherein voids are formed between the distribution layer and the riffled substrate.

31. The disposable article of claim 27, wherein each of said peaks and troughs run in the machine direction or toward said front and rear longitudinal edges.

32. The disposable absorbent article of claim 27, wherein each of said plurality of peaks extends in a non-linear manner between said front longitudinal edge and said rear longitudinal edge.

* * * * *